(12) United States Patent
Boussand et al.

(10) Patent No.: US 8,110,713 B2
(45) Date of Patent: Feb. 7, 2012

(54) PROCESS FOR PRODUCING PENTAFLUOROETHANE

(75) Inventors: Béatrice Boussand, Sainte Foy lès Lyon (FR); Sylvain Perdrieux, Charly (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 12/305,857

(22) PCT Filed: May 21, 2007

(86) PCT No.: PCT/FR2007/051304
§ 371 (c)(1),
(2), (4) Date: Apr. 27, 2010

(87) PCT Pub. No.: WO2007/147988
PCT Pub. Date: Dec. 27, 2007

(65) Prior Publication Data
US 2010/0210884 A1  Aug. 19, 2010

(30) Foreign Application Priority Data
Jun. 21, 2006  (FR) ...................................... 06 05525

(51) Int. Cl.
*C07C 17/087* (2006.01)
(52) U.S. Cl. ...................................... 570/169; 570/165
(58) Field of Classification Search .................. 570/134, 570/165, 169
See application file for complete search history.

(56) References Cited

U.S. PATENT DOCUMENTS
5,300,710 A  4/1994 Corbin

FOREIGN PATENT DOCUMENTS

| AU | B-53970/94 | * | 8/1994 |
| EP | 0609123 A1 | | 8/1994 |
| EP | 0754170 B1 | | 3/1999 |
| EP | 0760808 B1 | | 4/1999 |
| GB | 901297 A | | 7/1962 |

* cited by examiner

*Primary Examiner* — Noble Jarrell
*Assistant Examiner* — Karen Cheng
(74) *Attorney, Agent, or Firm* — Hunton & Williams LLP

(57) ABSTRACT

The present invention relates to a process for producing pentafluoroethane. More particularly, the subject of the invention is a continuous process for producing pentafluoroethane comprising (i) a step of fluorinating perchloroethylene (PER) with hydrofluoric acid, in the gas phase, in the presence of a catalyst, (ii) a step of separating the products issuing from step (i) in order to give a fraction of light products and a fraction of heavy products, comprising hydrofluoric acid, unreacted perchloroethylene and under-fluorinated products, and (iii) a step of pretreating the fraction of heavy products before recycling to step (i).

11 Claims, 1 Drawing Sheet

PROCESS FOR PRODUCING PENTAFLUOROETHANE

CROSS-REFERENCE TO RELATED APPLICATIONS

This application is the U.S. National Phase Application of International Application No. PCT/FR2007/051304, filed May 21, 2007, which claims the benefit of French Application No. FR 0605525, filed Jun. 21, 2006, the disclosures of each of which is hereby incorporated by reference.

FIELD OF THE INVENTION

The present invention relates to a process for producing pentafluoroethane. It relates more particularly to a continuous process for producing pentafluoroethane by fluorination of perchloroethylene (PER) in the gas phase in the presence of a catalyst.

BACKGROUND

One of the essential points of a gas-phase fluorination process is the stability of the catalyst.

Several solutions have been suggested to maintain the stability of the catalyst.

Thus, document EP 609123 describes a continuous process for catalytic fluorination of perchloroethylene in the gas phase by means of hydrofluoric acid in the presence of a mixed catalyst composed of nickel oxides, halides and/or oxyhalides and chromium oxides, halides and/or oxyhalides deposited onto a support consisting of aluminum fluoride or of a mixture of aluminum fluoride and alumina.

The stability of the catalyst is demonstrated in example 2 of this document, with a temperature of 350° C., at atmospheric pressure, an HF/PER ratio in the region of 7 and a contact time of 15 seconds.

During the fluorination of perchloroethylene by means of hydrofluoric acid in the presence of a catalyst, a mixture of compounds forms, with predominantly the compounds of the "F 120 series", namely F 121 ($CHCl_2$-$CCl_2F$), F 122 ($CHCl_2$-$CClF_2$), F 123 ($CHCl_2$-$CF_3$), F 124 ($CHFCl$—$CF_3$) and F 125 ($CHF_2$-$CF_3$), or isomers thereof. In addition to the compounds of the "F 120 series", the mixture contains in particular F 115 ($CF_3$-$CF_2Cl$), F 114a ($CF_3$-$CFCl_2$), F 114 ($CF_2Cl$—$CF_2Cl$), F 133a ($CH_2Cl$—$CF_3$) and olefins F 1111 ($CFCl$=$CCl_2$) and F 1112a ($CF_2$=$CCl_2$).

When the process is carried out under conditions where the conversion of the perchloroethylene (PER) is not complete, it is essential to recycle the unreacted PER in order to obtain a process for producing pentafluoroethane which is economically competitive. However, the recycling of the reactants is often accompanied by deactivation of the catalyst.

It has now been found that a pretreatment, before the recycling, of the stream leaving the reaction step makes it possible to maintain the stability of the catalyst.

SUMMARY OF INVENTION

The subject of the present invention is therefore a process for producing pentafluoroethane, comprising (i) a step during which perchloroethylene reacts with hydrofluoric acid, in the gas phase, in the presence of a catalyst, and (ii) a step of separating the products derived from the reaction step in order to give a fraction (A) of light products comprising hydrochloric acid and pentafluoroethane, and a fraction (B) of heavy products, characterized in that the fraction (B) comprising unreacted hydrofluoric acid, unreacted perchloroethylene and at least one compound chosen from trichlorodifluoroethane and olefinic compounds, such as F1111 and F1112a, is subjected to a catalytic pretreatment with an HF/organic compounds molar ratio of between 30 and 150, preferably between 60 and 130, at a temperature of between 280 and 400° C., preferably between 340 and 370° C., before being recycled to the reaction step.

DETAILED DESCRIPTION

Figure 1:
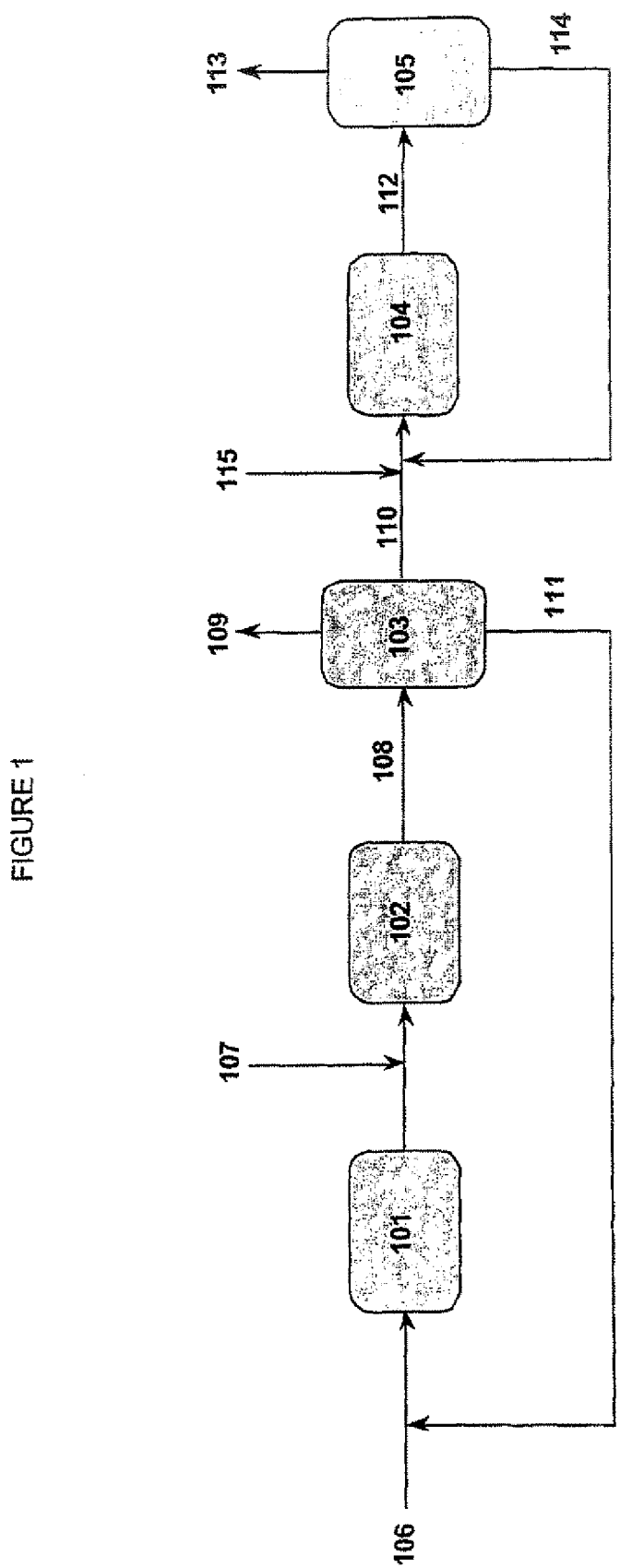
FIG. 1 is a schematic view of one embodiment of the invention illustrating the process for producing pentafluoroethane.

Although the pressure is not essential for the catalytic pretreatment, it is, however, preferred to operate at a pressure in the region of that of the reaction step (1), and advantageously at a pressure above that of the reaction step (i).

Depending on the operating conditions of the separating step, the dichlorotrifluoroethane and/or chlorotetrafluoroethane, formed in the reaction step, may be present either in the fraction (A) or in the fraction (B).

The fraction (A) may also comprise hydrofluoric acid, entrained in the form of an azeotrope with the fluoro carbon compounds such as pentafluoroethane, dichlorotrifluoroethane and chlorotetrafluoroethane.

The fraction (B) may be decanted so as to give a phase comprising essentially hydrofluoric acid and a phase comprising organic compounds. The two phases are subsequently sent to the pretreatment step.

Preferably, the catalyst of the pretreatment step is a fluorination catalyst. Advantageously the catalyst of the pretreatment step is of the same nature as that involved in the reaction step (i).

The HF/organic compounds molar ratio in the reaction step (i) is preferably between 5 and 60, advantageously between 7 and 30. The temperature may be between 300 and 400° C., preferably between 330 and 370° C.

The process according to the present invention is most particularly suitable when the reaction step is carried out at a pressure of between 1 and 15 bar absolute, preferably between 2 and 10 bar absolute, and advantageously between 5 and 9 bar absolute.

When the fraction (A) comprises dichlorotrifluoroethane and/or chlorotetrafluoroethane, it may be subjected, after separation of the hydrofluoric acid and, optionally, of the pentafluoroethane, to a fluorination step during which dichlorotrifluoroethane and/or chlorotetrafluoroethane react(s) with hydrofluoric acid in the gas phase, in the presence of a catalyst, so as to give pentafluoroethane. The unreacted dichlorotrifluoroethane and/or unreacted chlorotetrafluoroethane and the unreacted hydrofluoric acid can subsequently be recycled.

The HF/organic compounds molar ratio of the step of fluorinating the fraction (A) is preferably between 1 and 20, and advantageously between 2 and 10. This fluorination step is preferably carried out at a pressure in the region of that of the reaction step (i). The temperature is preferably between 300 and 400° C., and advantageously between 330 and 370° C.

Any fluorination catalyst may be suitable for the process of the present invention. The catalyst used preferably comprises the oxides, halides, oxyhalides or mineral salts of chromium, of aluminum, of cobalt, of manganese, of nickel, of iron or of zinc, and may be supported.

A chromium oxide ($Cr_2O_3$)-based catalyst, optionally including another metal in an oxidation state above zero and selected from Ni, Co, Mn and Zn, is preferably used. Advantageously, this catalyst may be supported on alumina, aluminum fluoride or aluminum oxyfluoride.

For this invention, mixed catalysts composed of nickel oxides, halides and/or oxyhalides and of chromium oxides, halides and/or oxyhalides, deposited on a support consisting of aluminum fluoride or of a mixture of aluminum fluoride and alumina, as described, for example, in patents FR 2 669 022 and EP-B-0 609 124, will be preferred.

When a mixed nickel/chromium catalyst is used, catalysts containing, by mass, from 0.5% to 20% of chromium and from 0.5% to 20% of nickel, and more particularly containing from 2% to 10% by mass of each of the metals, in a nickel/chromium atomic ratio of between 0.1 and 5, preferably in the region of 1, will be recommended.

Although not necessary for the fluorination reaction, it may be judicious to introduce, with the reactants, oxygen in a small amount. This amount may range, according to the operation conditions, between 0.02 and 2 mol % relative to the reactants going into the reactor. The introduction of the oxygen may be carried out continuously or sequentially. Oxygen may also be introduced in the pretreatment step.

The process according to the present invention may be carried out both continuously and batchwise, but it is preferred to operate continuously.

With reference to the single FIGURE, one embodiment of the process of the present invention is described below.

According to one embodiment, the pretreatment reactor (101) contains a catalyst and is fed with recycled stream (111) comprising unreacted hydrofluoric acid, unreacted perchloroethylene and at least one compound chosen from trichlorodifluoroethane and olefinic compounds such as F1111 and F1112a. The reactor (101) is fed with hydrofluoric acid also via the input (106). The reactor (102), containing a fluorination catalyst, is fed with perchloroethylene via the input (107) and, optionally, via the stream derived from the reactor (101), and with hydrofluoric acid via the stream leaving the reactor (101). The reaction products (108) are subsequently subjected to a separation series represented by (103) so as to give a fraction of heavy products which is recycled (111), a fraction of light products which, after separation of the HCl (109) and, optionally, of the F125 in the form of HF/F125 azeotrope, feeds the fluorination reactor (104), containing a catalyst, with dichlorotrifluoroethane and/or chlorotetrafluoroethane (110). This reactor (104) is fed with hydrofluoric acid via the input (115). The stream (110) may also contain hydrofluoric acid. The reaction products are subsequently subjected to a separating step (105) in order to give a fraction of light products (113) comprising hydrochloric acid, pentafluoroethane and, optionally, hydrofluoric acid in the form of an azeotrope with pentafluoroethane, and a fraction of heavy products (114) comprising essentially hydrofluoric acid, dichlorotrifluoroethane and/or chlorotetrafluoroethane which are (is) unreacted, which is recycled to the reactor (104).

According to one variant, a common separating device may be used for the products derived from the reactors (102) and (104). In this case, the reaction products (112) are sent back to (103) instead of (105).

Experimental Section

The catalyst used is a mixed nickel/chromium catalyst with an Ni/Cr atomic ratio=1, supported on prefluorinated alumina, and is prepared by impregnation of solutions of nickel salt and chromic salt. After impregnation and drying, the solid is subjected to treatment at a temperature between 320 and 390° C., in the presence of a mixture of hydrofluoric acid and nitrogen (concentration by volume of 5% to 10% of this acid in nitrogen).

The examples were carried out using a fluorination pilot, consisting of a fluorination reactor (102), a distillation column and, optionally, a pretreatment reactor (101). The reactants, in the gas phase, are fed continuously (perchloroethylene and hydrofluoric acid) into an Inconel fluorination reactor (102) containing 200 ml of catalyst. At the reactor output, a distillation column makes it possible to separate, on the one hand, the reaction products, such as F123, F124, F125, HCl or HF (entrained in the form of an azeotrope with the organic compounds), from, on the other hand, the unconverted reactants and under-fluorinated products (PER, HF in excess, F122, F1111). At the foot of the column, after decanting of a liquid phase comprising essentially HF and of an organic phase, the 2 phases are recycled separately to the reactor.

The level of organic phase is kept constant by withdrawing.

In the example in accordance with the invention, the recycled stream (consisting of the two phases after decanting) is subjected to a pretreatment in the presence of 56 ml of catalyst contained in an Inconel reactor (101). In this case, all the hydrofluoric acid necessary for the various steps is fed into the reactor (101) and most of the perchloroethylene is introduced into the reactor (102).

Air is introduced into the reactors (101) and (102) in an amount such that it corresponds to the molar ratio indicated below.

In all the examples described below, the compositions of the recycled HF and organic compound phases are stabilized at compositions close to:

organic phase:
PER: 70 mol %
F122: 21 mol %
F1111: 7 mol %
various (F123, F122a, F121): 2 mol %

HF phase:
HF: 98 mol %
various (PER, F122): 2 mol %

In each example, we calculate:
the conversion per pass of PER=percentage ratio between the PER consumed and the PER entering the PER fluorination reactor
the production of F123+F124+F125 in mmol/h.

Example without Pretreatment

The operating conditions in the PER fluorination reactor are the following:
oven temperature regulated at 310° C.
pressure: 7 bar abs
HF/organic compounds molar ratio=8
$O_2$/organic compounds molar ratio=5%
contact time=35 s The results are given in the table below:

| Duration (h) | Conversion of PER (%) | Production of F123 + F124 + F125 (mmol/h) |
| --- | --- | --- |
| 20 | 94 | 306 |
| 188 | 92 | 301 |
| 259 | 88 | 285 |
| 380 | 86 | 277 |
| 476 | 77 | 246 |

Example in Accordance with the Invention

The operating conditions for the pretreatment are the following:

oven temperature regulated at 350° C.
pressure: 7 bar abs
HF/organic compounds molar ratio=96
O$_2$/(HF+organic compounds) molar ratio=0.65%
contact time=10 s
The operating conditions in the PER fluorination reactor are the following:
oven temperature regulated at 310° C.
pressure: 7 bar abs
HF/organic compounds molar ratio=8
O$_2$/organic compounds molar ratio=5%
contact time=35 s
The results are given in the table below:

| Duration (h) | Conversion of PER (%) | Production of F123 + F124 + F125 (mmol/h) |
|---|---|---|
| 24 | 94 | 308 |
| 220 | 93 | 302 |
| 463 | 93 | 303 |
| 612 | 94 | 307 |
| 877 | 92 | 300 |
| 1015 | 93 | 304 |

The invention claimed is:

1. A process for producing pentafluoroethane comprising the steps of:
   (i) reacting perchloroethylene with hydrofluoric acid (HF) in the gas phase and in the presence of a first fluorination catalyst
   (ii) separating the products derived from step (i) to yield
      a fraction (A) of light products comprising hydrochloric acid and pentafluoroethane, and
      a fraction (B) of heavy products comprising unreacted hydrofluoric acid, unreacted perchloroethylene, and at least one compound comprising trichlorodifluoroethane or olefinic compounds;
   (iii) reacting fraction (B) with hydrofluoric acid (HF) in the presence of a second fluorination catalyst at a temperature ranging from 280 to 400° C. prior to recycling the products of step (iii) to step (i),
      wherein the HF/organic compounds molar ratio in step (iii) ranges from 30 to 150.

2. The process of claim 1, wherein said olefinic compounds comprise CFCl=CCl$_2$ and/or CF$_2$=CCl$_2$.

3. The process of claim 1, wherein said molar ratio ranges from 60 to 130.

4. The process of claim 1, wherein said temperature ranges from 340 to 370° C.

5. The process of claim 1, wherein said fraction (A) further comprises dichlorotrifluoroethane and/or chlorotetrafluoroethane.

6. The process of claim 5, wherein after separation of said hydrochloric acid and, optionally, after separation of said pentafluoroethane, said fraction (A) is subjected to a fluorination step with hydrofluoric acid, in the gas phase and in the presence of a cytalyst with further comprising separating hydrochloric acid from fraction (A) before reacting fraction (A) with hydrofluoric acid in the gas phase and in the presence of a third fluorination catalyst.

7. The process of claim 1, wherein oxygen is introduced in steps (i) and (iii).

8. The process of claim 1 wherein said first fluorination catalyst and/or said second fluorination catalyst comprises.

9. The process of claim 8, wherein said chromium-oxide-based catalyst includes another metal in an oxidation state above zero, said metal comprising Ni, Co, Mn, Zn, or mixtures thereof.

10. The process of claim 1, further comprising adding perchloroethylene to the products of step (iii) prior to recycling to step (i).

11. The process of claim 6, further comprising separating pentafluoroethane from fraction (A) before reacting fraction (A) with hydrofluoric acid in the presence of the third fluorination catalyst.

* * * * *